(12) United States Patent  (10) Patent No.: US 12,296,161 B2
Kryzanski  (45) Date of Patent: May 13, 2025

(54) SUBDURAL SOUND WITH A RECEIVING CHANNEL

(71) Applicant: Hemisphere Medical LLC, Chestnut Hill, MA (US)

(72) Inventor: James Kryzanski, Chestnut Hill, MA (US)

(73) Assignee: Hemisphere Medical LLC, Chestnut Hill, MA (US)

( * ) Notice: Subject to any disclaimer, the term of this patent is extended or adjusted under 35 U.S.C. 154(b) by 533 days.

(21) Appl. No.: 17/474,716

(22) Filed: Sep. 14, 2021

(65) Prior Publication Data

US 2023/0077799 A1  Mar. 16, 2023

(51) Int. Cl.
*A61N 1/05* (2006.01)
*A61N 1/36* (2006.01)

(52) U.S. Cl.
CPC ....... *A61N 1/0531* (2013.01); *A61N 1/36064* (2013.01)

(58) Field of Classification Search
CPC .. A61N 1/0526; A61N 1/0529; A61N 1/0531; A61N 1/36; A61N 1/3605; A61N 1/36064
See application file for complete search history.

(56) References Cited

U.S. PATENT DOCUMENTS

| | | | |
|---|---|---|---|
| 5,044,368 A | 9/1991 | Putz | |
| 6,024,702 A | 2/2000 | Iversen | |
| 6,978,180 B2 | 12/2005 | Tadlock | |
| 8,364,237 B2 | 1/2013 | Stone et al. | |
| 9,820,668 B2 | 11/2017 | Hua | |
| 10,912,937 B2 | 2/2021 | Kryzanski | |
| 2002/0022873 A1 | 2/2002 | Erickson et al. | |
| 2003/0009207 A1 | 1/2003 | Paspa et al. | |
| 2004/0122360 A1 | 6/2004 | Waldhauser et al. | |
| 2005/0090885 A1 | 4/2005 | Harris et al. | |
| 2005/0234507 A1 | 10/2005 | Geske et al. | |
| 2006/0122677 A1 | 6/2006 | Vardiman | |
| 2006/0136008 A1 | 6/2006 | Tadlock | |
| 2010/0179518 A1 | 7/2010 | Ludvig et al. | |
| 2010/0241100 A1 | 9/2010 | Blumenfeld et al. | |

(Continued)

FOREIGN PATENT DOCUMENTS

WO   2011084788 A2   7/2011

OTHER PUBLICATIONS

Dixi Medical, "Microdeep depth electrode." Retrieved from http://www.diximedical.com/en/microsdeep-depth-electrode on Apr. 9, 2018, 10 pages.

(Continued)

*Primary Examiner* — Christopher A Flory
(74) *Attorney, Agent, or Firm* — Occhiuti & Rohlicek LLP

(57) ABSTRACT

Disclosed are devices, electrodes, systems, methods, and other implementations, including a subdural sound that includes an elongated body configured to be placed within a subdural space of a brain area of a patient, with the elongated body defining a receiving channel to receive a displaceable electrode to be tangentially placed at a target site in the subdural space. The subdural sound further includes a curved tip at a distal end of the elongated body, the curved tip configured for angled insertion into the subdural space of the patient to advance the elongated body to the target site in the subdural space.

15 Claims, 8 Drawing Sheets

(56) References Cited

U.S. PATENT DOCUMENTS

| | | | | |
|---|---|---|---|---|
| 2012/0209283 | A1* | 8/2012 | Zhu | A61N 1/0553 |
| | | | | 606/129 |
| 2013/0085361 | A1* | 4/2013 | Mercanzini | A61B 5/4041 |
| | | | | 600/377 |
| 2014/0025039 | A1* | 1/2014 | Rajendran | A61M 19/00 |
| | | | | 604/512 |
| 2014/0121674 | A1* | 5/2014 | Staunton | A61B 17/3468 |
| | | | | 606/129 |
| 2015/0112360 | A1* | 4/2015 | Pellinen | A61B 5/291 |
| | | | | 606/129 |
| 2016/0089515 | A1* | 3/2016 | Hansen | A61M 25/09 |
| | | | | 604/528 |
| 2016/0256062 | A1 | 9/2016 | Greger et al. | |
| 2017/0007825 | A1 | 1/2017 | Thakkar et al. | |
| 2017/0173340 | A1 | 6/2017 | Gupte et al. | |
| 2019/0308008 | A1* | 10/2019 | Kryzanski | A61N 1/0529 |
| 2020/0094049 | A1 | 3/2020 | Kryzanski | |

OTHER PUBLICATIONS

Greger, et al., "A chronically implantable, hybrid cannula-electrode device for assessing the effects of molecules on electrophysiological signals in freely behaving animals." J. Neurosci Methods. Jul. 30, 2007, 163(2): 321-325.

Du Hoffmann et al., "An inexpensive drivable cannulated microelectrode array for simultaneous unit recording and drug infusion in the same brain nucleus of behaving rats," J. Neurophysiol., Aug. 2011; 106(2): pp. 1054-1064.

Kaiboriboon et al., "Epilepsy surgery in the United States: Analysis of data from the National Association of Epilepsy Centers." Epilepsy Research 116 (2015) pp. 105-109.

Rolston et al., "Rate and Complications of Adult Epilepsy Surgery in North America: Analysis of Multiple Databases." Accepted Manuscript to Appeal in Epilepsy Research, Accepted date: May 5, 2016, 31 pages. http://dx.doi.org/10.1016/j.eplepsyres.2016.05.001.

* cited by examiner

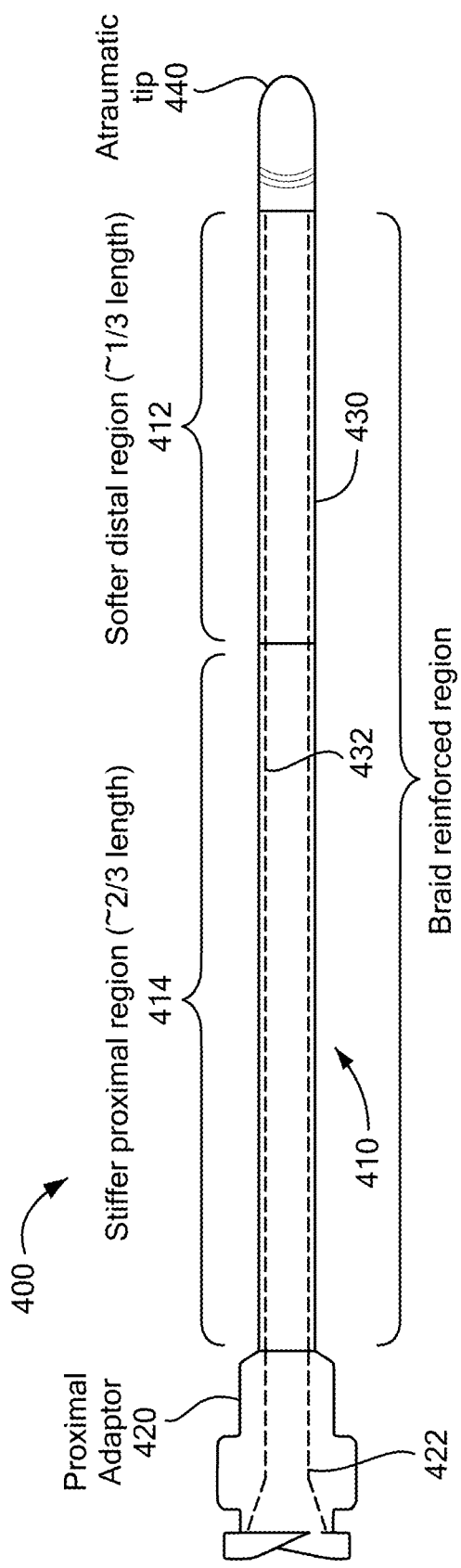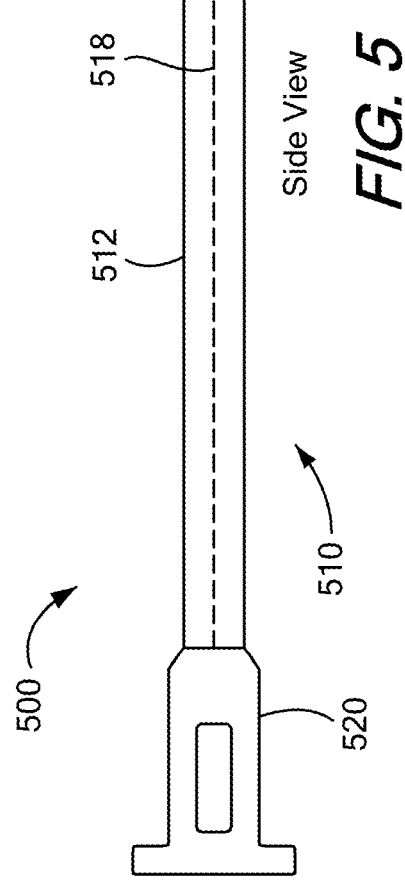

SUBDURAL SOUND WITH A RECEIVING CHANNEL

BACKGROUND

Epilepsy will affect 1 in 26 Americans over their lifetimes and in 30% of cases medications are not effective in controlling the seizures. In these 'medically refractory' cases, surgical options should be considered given the malignant nature of uncontrolled seizures. Recent studies have concluded that epilepsy surgery is underutilized. Nevertheless, surgical procedures for intracranial electrode placement are common and increasing. Furthermore, recent technological advances such as responsive neurostimulation with the Neuropace™ system provide potential surgical options for patients who have seizures coming from multiple or eloquent brain areas and were previously not candidates. These patients nearly always require initial intracranial electrode monitoring. Subdural electrodes are also used in cyberprosthetic devices where surface electrode recordings are decoded and used to generate speech, movement, and other functions in patients with neurologic injury. Additional applications where subdural electrodes may be used include responsive neurostimulation to treat epilepsy and cortical stimulation for chronic pain. These applications often rely on conventional subdural grid technology.

The crucial aspect of surgical evaluation is identifying the area(s) of the brain responsible for seizures, and this is often done by intracranial electrode placement. Subdural, or brain surface, electrodes are often used in patients with refractory epilepsy to determine the seizure focus. The subdural space is the area between the brain surface and the dura, or fibrous covering, of the brain. The 'ictal zone', or area of seizure onset, is determined by seizure recording by electrodes covering the area. Therefore, surgeons try to cover a large area of the cortex with electrodes in order to maximize the chance of finding the ictal zone. The current technique for placing a subdural electrode array involves surgery to remove a significant piece of the skull and then lay a subdural grid and numerous strip electrodes on the brain surface. The invasiveness and risk of this procedure is considerable.

Another technique that is used for the placement of brain electrodes is based on using stereo-EEG, where electrodes are placed into the brain itself and not on the brain surface through small skull drill holes in computer-determined trajectories. Though superficially less invasive than subdural electrode arrays, this technique requires multiple penetrations of the brain and does not optimally record from the brain surface, where most seizures arise.

SUMMARY

Disclosed are devices, systems, methods, and other implementations to facilitate placement of displaceable electrodes (e.g., subdural electrodes) through a small drill hole in the skull. The implementations include placing a subdural sound (also referred to as a "subdural depth sound", a "subdural depth sounding instrument," a "guiding probe," a "subdural probe," and/or a "guiding device") within the subdural space in a patient's brain, with the leading end (also referred to as distal end) of the subdural sound being located near the destination location where a subdural electrode is to be deployed. The subdural sound includes a receiving channel through which subdural electrodes are guided to the leading end of the subdural sound (already inserted so that the leading end is located in the subdural space), whereupon the subdural sound can be retraced while leaving the electrode that was guided through the receiving channel at approximately the destination location. The subdural sound includes a curved tip, located at a distal end of the body of the subdural sound, that is configured to be inserted into a subdural space of a patient, and to negotiate the acute angles to position the subdural sound's body tangentially to the dura tissue so that the subdural sound can be advanced along the surface of the dura tissue to its destination position. The subdural sound may be constructed to have certain material and structural properties that facilitate its advancement in the subdural space to the destination location, including a variable rigidity profile along the length of the sound, and the use of support wires to allow flexible movement in one direction but inhibit movement in other directions.

Advantageously, the structural features of the subdural sound described herein allow the subdural sound to advance in the subdural space with minimal resistance and with reduced risk of injuring the brain tissue (through accidental piercing or abrasion of the tissue), and can thus be guided to the destination location by gentle pushing/prodding (by a surgeon) of the sound to the desired location in the subdural space, without requiring elaborate navigation equipment or imaging apparatus. Nevertheless, in some embodiments, imaging equipment may be used to more accurately guide the subdural sound through the subdural space. For example, image data may be obtained via an optic fiber included with the subdural sound. Alternatively, the location of the sound can be determined through external imaging apparatus (e.g., X-Ray, MRI apparatus) when the sound is properly fitted with, for example, radiopaque indicators.

The subdural sound generally includes a distance determination mechanism, e.g., implemented through the inclusion of markings, that indicate the length of sound within the patient's body. Based on the determined length of the sound body within the subdural space, an appropriately-sized electrode (which may be conventional subdural electrodes, or electrodes such as those described in, for example, U.S. Pat. No. 10,912,937, entitled "Methods and devices for guided subdural electrode array placement," the content of which is hereby incorporated by reference in its entirety) is selected and fitted within the receiving channel of the subdural node. The selected electrode is then pushed along the receiving channel of the now deployed sound.

The use of the subdural sounds described herein, and the procedures for placing electrodes in the subdural space using such subdural sounds, offer several advantages, including:

a) Allowing relatively easy insertion and advancement of the sound (and thus of the electrode subsequently fitted in the receiving channel of the sound) into the subdural space, at sharp angles and turns. The unique structure and properties of the subdural sound devices described herein reduce the risk of brain injury during placement.

b) Traditionally, it has been difficult to accurately predict the electrode length required as sometimes unexpected obstacles (veins, adhesions, etc.) would impede passage through the subdural space. Without knowing the required electrode length, it is necessary to pass several electrodes into the subdural space before a suitable electrode length is determined. This is suboptimal because every additional passage increases risk of injury to the brain. The use of the subdural sounds described herein avoids this problem because the electrode length required for placement at a certain target site is indicated by markings on the sound showing the length of the portion of the subdural sound that was inserted and advanced to the target site. The appropriate electrode can be selected without any unnecessary passes through the subdural space.

In some of the embodiments described herein, a thin and flexible subdural sound can navigate 90 degree turns under the bone edge into the subdural space. Once the sound is advanced into position, it creates a stable platform through which to pass a flexible electrode. The risk of brain injury is greatly reduced since the subdural sound substantially encases (and in some embodiments completely contains) the electrode within a receiving channel defined in the subdural sound, as the electrode is advanced to a distal opening in the subdural sound through which the electrode is deployed for tangential placement on the target tissue (be it the dura mater or some other body tissue). Since the resistance in the subdural space is minimal, the subdural sound device itself is configured/implemented to have a softness and flexibility whereby it would be unlikely to penetrate the brain even if directed perpendicularly with reasonable force (it would curl at the tip instead of penetrating). Through placement of shape memory support wires within the body of the subdural sound, and appropriate design of the shape and rigidity characteristics of the sound device, the devices described herein are configured to inhibit perpendicular movement (i.e., in a direction normal to the surface of the dura mater) of the device (unlike, for example, a tubular catheter), and generally travels only in the intended directions.

In some embodiments, the electrodes deployed through the devices and approaches described herein form a radial electrode potential array that achieves extensive cortical electrode coverage and that generally requires only a single small burr hole drilled in the skull. An unlimited number of potential array configurations are possible by varying the burr hole size, location, and the number/direction of electrodes deployed via the sound devices described herein.

Thus, in some variations, a subdural sound is provided that includes an elongated body configured to be placed within a subdural space of a brain area of a patient, with the elongated body defining a receiving channel to receive a displaceable electrode to be tangentially placed at a target site in the subdural space. The subdural sound also includes a curved tip at a distal end of the elongated body, the curved tip configured for angled insertion into the subdural space of the patient to advance the elongated body to the target site in the subdural space.

Embodiments of the subdural sound may include at least some of the features described in the present disclosure, including one or more of the following features.

The elongated body may include a flexible ovalized lumen defining the receiving channel.

The flexible ovalized lumen may include an exterior oval wall constructed from a braid-reinforced polymer, with two or more support wires embedded in the exterior oval wall and extending along substantially a length of the subdural sound, the two or more support wires configured to prevent kinking of the flexible ovalized lumen during advancement of the flexible ovalized lumen in the subdural space.

The two or more support wires may cause the elongated body to have a reduced level of flexibility in one or more planes defined by the two or more support wires, compared to other planes intersecting the elongated body of the subdural sound, with the reduced level of flexibility in the one or more planes defined by the two or more support wires restricting degree of deflection of the elongated body in the one or more planes while allowing partial deflection of the elongated body in at least one of the other planes intersecting the elongated body.

The two or more support wires may be constructed using one or more shape-memory materials.

The one or more shape-memory materials may include a Nickel Titanium (nitinol) material.

The elongated body may include an exterior wall fully enclosing, in cross-section, the receiving channel.

The elongated body may include a plurality of adjacent regions along a length of the subdural sound, the plurality of adjacent regions each having respective different rigidity characteristics.

A distal portion of the elongated body may be more flexible than another portion of elongated body.

The curved tip may include a first side with a curving profile defined in relation to a first axis of the elongated body, a second side with a substantially flat profile in relation to the first axis, and third and fourth sides defining a tapering profile in relation to a second axis of the elongated body.

The curved tip may include a radiopaque material.

A proximal end of the elongated body may be couplable to an irrigation adapter connectable to an irrigation mechanism that directs irrigation fluid through the receiving channel defined in the elongated body of the subdural sound to facilitate displacement of subdural sound through the subdural space.

The irrigation adapter couplable to the elongated body may include a Luer lock adapter.

The curved tip may be a shaped-set portion integrally extending from the elongated body.

The subdural sound may further include a distance determination mechanism configured to indicate penetration distance of the subdural sound into the subdural space.

The distance determination mechanism may include a plurality of radiopaque markings disposed along the elongated body to indicate the penetration distance of the subdural sound.

In some variations, a system is provided that includes a subdural sound including an elongated body configured to be placed within a subdural space of a brain area of a patient, the elongated body defining a receiving channel, and a curved tip at a distal end of the elongated body, the curved tip configured for angled insertion into the subdural space of the patient to advance the elongated body to a target site in the subdural space. The system additionally includes an electrode comprising an elongated structure, a plurality of electrical contacts disposed on a substantially flat first side of the elongated structure, with a leading end of the electrode being fitted within a proximal end of the receiving channel of the subdural sound so as to be advanced via the receiving channel, when the subdural sound is placed at the target site within the subdural space, to the target site for tangential placement of the electrode on target tissue in the subdural space.

Embodiments of the system may include at least some of the features described in the present disclosure, including at least some of the features described above in relation to the subdural sound, as well as one or more of the following features.

The elongated body of the subdural sound may include a flexible ovalized lumen defining the receiving channel.

The flexible ovalized lumen may include an exterior oval wall constructed from a braid-reinforced polymer, with two or more support wires embedded in the exterior oval wall and extending along substantially a length of the subdural sound, the two or more support wires configured to prevent kinking of the flexible ovalized lumen during advancement of the flexible ovalized lumen in the subdural space.

The two or more support wires may cause the elongated body to have a reduced level of flexibility in one or more planes defined by the two or more support wires, than in other planes intersecting the elongated body of the subdural sound, with the reduced level of flexibility in the one or more planes defined by the two or more support wire restricting degree of deflection of the elongated body in the one or more planes while allowing partial deflection of the elongated body in at least one of the other planes intersecting the elongated body.

The two or more support wires may be constructed from a Nickel Titanium (nitinol) material.

The elongated body of the subdural sound may include a plurality of adjacent regions along a length of the subdural sound, the plurality of adjacent regions each having respective different rigidity characteristics.

The curved tip may include a first side with a curving profile defined in relation to a first axis of the elongated body, a second side with a substantially flat profile in relation to the first axis, and third and fourth sides defining a tapering profile in relation to a second axis of the elongated body.

The elongated structure of the electrode may include a chain of body sections, wherein at least some of the body sections include tapered ends along a longitudinal axis of each of the at least some of the body sections, and wherein each of the plurality of electrical contacts is disposed at a respective different one of the body sections.

The electrode may include multiple folded electrode strips defining the elongated structure, the multiple folded electrode strips configured to be unfolded for deployment over the target tissue in the subdural space.

The system may further include an irrigation adapter coupled to a proximal end of the elongated body of the subdural sound, the irrigation adapter being connectable to an irrigation mechanism, and configured to direct irrigation fluid through the receiving channel defined in the elongated body of the subdural sound to facilitate displacement of subdural sound through the subdural space.

The system may further include a wedge implement configured to facilitate insertion of the elongated body of the subdural sound into the subdural space at angles, formed by a longitudinal axis of the elongated body and a tangential plane of the subdural space, in a range of 70°-110°, the wedge implement configured to receive the curved tip of the subdural sound for slidable displacement of the curved tip across the wedge implement to allow the curved tip to slidably enter the subdural space.

In some variations, a method is provided that includes forming a hole in a skull of a patient to access target tissue in a subdural space in a brain area of the patient, and directing through the hole a subdural sound comprising an elongated body, defining a receiving channel, and a curved tip at a distal end of the elongated body, to a target site in the subdural space, the curved tip configured for angled insertion into the subdural space of the patient. The method additionally includes fitting into the receiving channel defined in the elongated body of the subdural sound an electrode comprising a plurality of electrical contacts, and advancing the electrode through the receiving channel defined in the elongated body of the subdural sound towards the distal end of the subdural sound at a target site for placement of the electrode tangential to the target tissue in the subdural space of the patient.

Embodiments of the method may include at least some of the features described in the present disclosure, including at least some of the features described above in relation to the subdural sound and the system, as well as one or more of the following features.

The method may further include withdrawing the subdural sound from the subdural space following placement of the electrode at the target tissue.

The method may further include withdrawing the subdural sound from the subdural space while applying pressure to a proximal end of the electrode to keep the electrode in the tangential placement at the target tissue, and repeating the directing, fitting, and advancing for one or more other subdural sounds and/or for one or more electrodes, at respective one or more locations in the subdural space to form an electrode array spanning at a least a portion of a patient's cerebral tissue.

Repeating the directing, fitting, and advancing for one or more other subdural sounds and/or for one or more electrodes to form the electrode array may include deploying the electrode array to form one or more of, for example, a brain-computer interface, and/or a brain disorder monitoring and treating array.

Directing the subdural sound to the target tissue may include determining penetration distance of the subdural sound into the subdural space based on markings disposed on the elongated body of the subdural sound, and fitting one of a plurality of available electrodes with a length selected based on the determined penetration distance.

The method may further include delivering irrigation fluid via an irrigation adapter coupled to a proximal end of the elongated body of the subdural sound, and through the receiving channel defined in the elongated body of the subdural sound.

The electrode may include multiple folded electrode strips, and the method may further include unfolding the multiple folded electrode strips to deploy the unfolded electrode strips over the target tissue.

The electrode may include an electrode sheet with multiple electrical contacts disposed on the sheet. Fitting the electrode into the receiving channel may include fitting a first edge section of the electrode sheet into the receiving channel of the subdural sound. Advancing the electrode through the receiving channel may include advancing the first edge section of the electrode sheet through the receiving channel for placement of the first edge section of the electrode tangential to the target tissue in the subdural space of the patient. The method may further include directing another subdural sound through the hole for placement of the other subdural sound at another location in the subdural space of the patient while the subdural sound remains at the target site to anchor the first edge section at substantially the target tissue, fitting another edge section of the electrode sheet into another receiving channel of the other subdural sound, and advancing the other edge section of the electrode sheet to the other location in the subdural space of the patient.

The method may further include fitting a wedge implement through the hole, the wedge implement configured to facilitate insertion of the elongated body to the subdural space at angles, formed by a longitudinal axis of the elongated body and a tangential plane of the subdural space, in a range of 70°-110°. Directing through the hole the subdural sound may include placing the curved tip on the wedge implement fitted through the hole, and slidably displacing the curved tip across the wedge implement to allow the curved tip to slidably enter the subdural space.

Other features and advantages of the invention are apparent from the following description, and from the claims.

BRIEF DESCRIPTION OF THE DRAWINGS

These and other aspects will now be described in detail with reference to the following drawings.

FIG. 4 is a top-view diagram of a subdural sound that includes a plurality of adjacent regions, with each such region having different rigidity characteristics.

FIG. 5 is a side-view diagram of an example subdural sound.

Like reference symbols in the various drawings indicate like elements.

DESCRIPTION

Figure 1:
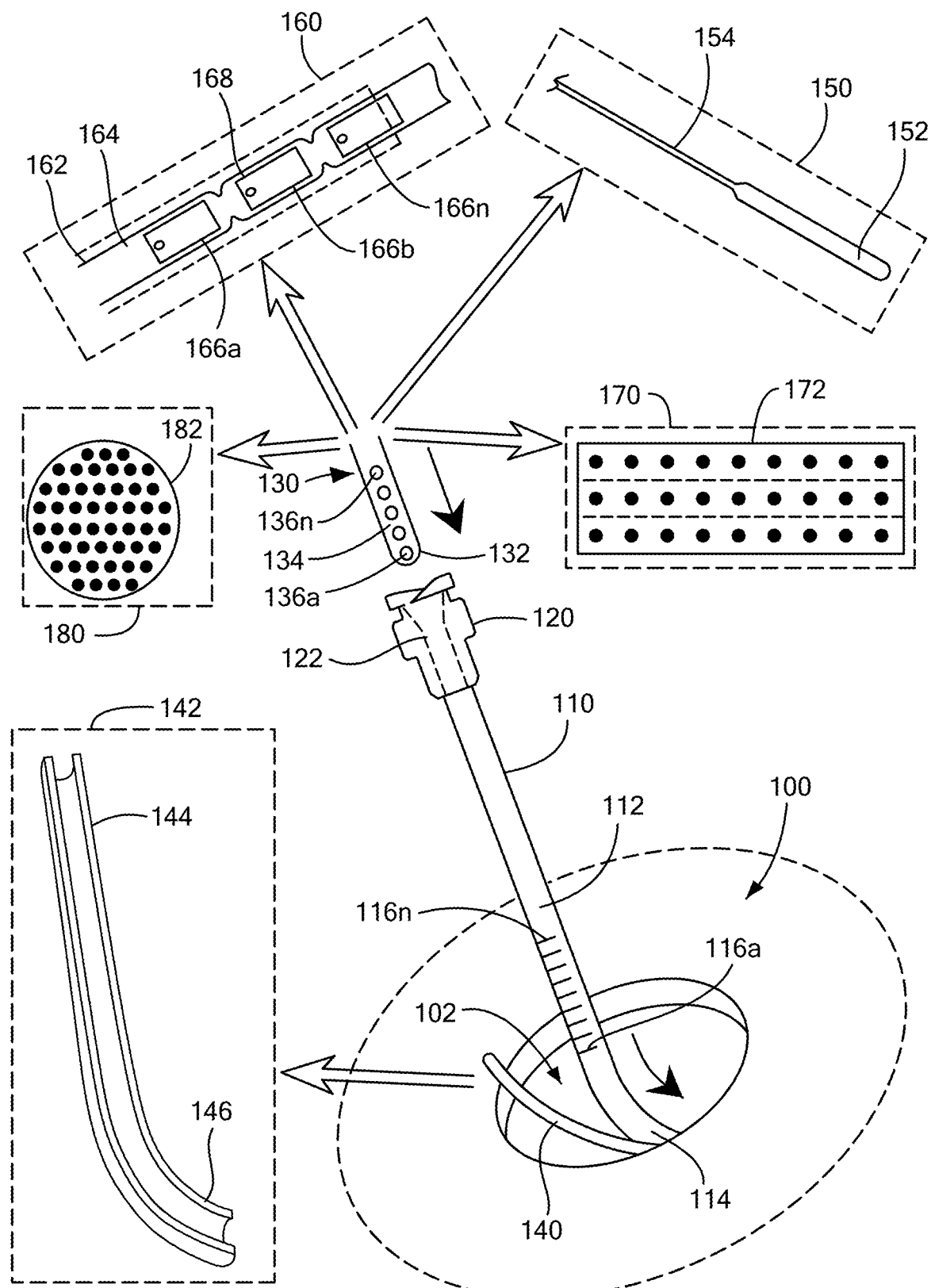
FIG. 1 is a diagram of an example system that includes a subdural sound for placement of one or more electrodes in the brain.

Disclosed herein are methods, systems, devices, and other implementations to tangentially place one or more subdural electrodes (e.g., so as to form an array of electrodes) on cerebral tissue in the subdural space. The implementations described herein include a subdural sound (probe) device comprising an elongated body with a curved tip and a receiving channel, defined in the elongated body, through which the subdural electrodes can be fitted to guide them to a desired location. The subdural sound is structured to flexibly bend in some directions (relative to the longitudinal axis of the elongated body of the sound) but to maintain some rigidity (and resist bending) in response to same level of force applied in other directions. The sound, once manipulated to slide tangentially to the dura mater (by actuating the sound so that the curved tip is slidably inserted/wedged into the subdural space), and guided through the subdural space via a moderate application of pushing force, advances through the subdural space to a desired location. A subdural electrode is fitted into the receiving channel and safely pushed along the receiving channel to a distal opening at leading end of the elongated body of the sound (the distal opening may be at a distal end of the curved tip when the curved tip is an integral part of elongated body). Once the electrode reaches the distal opening of the device, the sound can be retracted, thus deploying the electrode so that the electrode comes in directed contact with the brain tissue at the target site, by, for example, applying inward force on the proximal (trailing) end of the electrode, while pulling out the sound. The process can be repeated by introducing the same retracted sound, or a different sound, through the same burr-hole to another target site in the subdural space, and advancing another electrode towards the distal opening of the inserted sound.

The one or more subdural sounds that are used to deploy electrodes in the subdural space can be constructed from lubricious material, and fabricated so that the elongated body has a varying flexibility profile (e.g., is softer at the distal/leading region of the sound, and stiffer at the sound's proximal/trailing region). The variable stiffness profile, along with the curved tip extending from the distal end of the sound, allows for relatively simple nudging motion and actuation of the sound (by agitating the proximal end of the sound) to negotiate the initial sharp angle entry needed to place the curved tip in the subdural space. The subdural sound may optionally be fitted with optical, electrical, or chemical sensors that confirm location in the subdural space during passage. Additional optional features may include implementations where the deployed electrodes are used for uses other than epilepsy, including for cortical stimulators and cyberprostheses (e.g., to form the brain-machine interface). In these situations the electrodes may be placed as part of a permanent prosthesis and not just for temporary monitoring.

Thus, with reference to FIG. 1, a diagram of a system 100 used for placement of one or more displaceable electrodes in the brain (e.g., tangential to the surface of the dura mater tissue) is shown. As illustrated, in order to achieve minimal bone exposure, electrodes to be deployed on brain tissue (such as the schematically shown flexible electrode 130) have to navigate acute angled paths/trajectories in order to allow placement of such an electrode tangential to the brain surface. The placement of such an electrode is achieved by inserting a flexible subdural sound 110 (also referred to as a subdural probe) via an opening or hole (burr-hole) 102 drilled in the skull. As shown in FIG. 1, the flexible sound comprises a curved or bent distal (leading) tip 114 extending from an elongated body 112 of the subdural sound 110. The tip may be an integral part of the subdural sound (i.e., the elongated body 112 and the curved tip may constitute a single continuous piece instead of two separate attachable parts), but the subdural sound may have variable rigidity characteristics such that the distal region of the sound (which may include the curved tip 114 and part of the relatively straight elongated body 112) is more flexible than a proximal (trailing) region of the subdural array. The variable rigidity allows the distal region to be deformed and to adjustably bend as needed to have the curved tip fit within the subdural space underneath a patient skull (potentially needing the sound to initially be advanced at an angle of 70-90° relative to the normal to the skull.

In some implementations, the sound 110 may be equipped with one or more optical fibers/wires that attach to a light-capture device (e.g., camera). For example, such optical fibers (not shown in FIG. 1) may extend to the distal end of the subdural sound 110 at around the bent distal tip 114. A light source may deliver light via one such optical fibers, whose end is located near the leading end of the sound, to illuminate the area through which the sound is advancing, while another optical fiber optical wire may deliver reflected light back to the light-capture device, via a lens assembly, to allow the operator to view the area where the electrode is located. In other implementations, the sound is equipped with an electrical or chemical sensor at the tip that confirms the subdural location of the sound during navigation as the electrical and chemical properties of the subdural space differ from that of the brain.

The subdural sound 110 may also include, in some embodiments, a distance determination mechanism that is configured to indicate penetration distance of the subdural sound within the subdural space (or within some other target tissue to which an electrode is to be advanced). By knowing the length/depth of the sound (e.g., as measured from the entry point into the body, to the leading point of the sound, proximate the target site), an electrode of an appropriate length (e.g., substantially equal to the determined length/depth of the sound) can be used, thus avoiding having to use an improperly sized electrode (which could result in having to fold or cut the excess length of the electrode, or snaking in a different electrode with a different length). In some examples, the distance determination mechanism may be realized as a plurality of markings 116a-n disposed along the elongated body 112 of the subdural sound 110 (the use of markings to indicate depth is reminiscent of markings used in a depth sound used to measure water depth). In some embodiments, one or more of the plurality of markings 116a-n may include radio-opaque markings that can be detected and/or tracked using various imaging technologies (e.g., X-ray). In some embodiments, the subdural sound may be at least 20 cm in length, and may include a radio-opaque strip or filament throughout.

As further shown in FIG. 1, the system 100 includes a subdural electrode 130, which may be a customized electrodes or commercially available subdural electrode, that includes a plurality of electrical contacts (136a-n) disposed on a substantially flat first side 134 of an elongated structure 132 of the electrode 130. The electrode 130 is dimensioned so that it fits, and can be displaced, within a receiving channel defined in the elongated body of the subdural sound (the receiving channel is not shown in FIG. 1, but is illustrated as a receiving channel 432 of a subdural sound 410 shown in FIG. 4). FIG. 1 also includes a further schematic illustration of the electrode 130 within inset 150. As further shown in the inset 150, the electrode includes a contact section 152 on which contacts, such as the contacts 136a-n, are disposed on the surface (not illustrated in the inset 150) of the section 152 that contacts the brain tissue, and a narrowed (and typically longer) tail section 154 that a user (doctor or technician) handles to push the displaceable electrode within the receiving channel of the subdural sound, or to otherwise advance the electrode in the medium or device in which the electrode is deployed. The electrode may, in some embodiments, be fitted directly through a trailing open end of the receiving channel of the subdural sound. The receiving channel may, however, be relatively narrow, making fitting of the electrode somewhat cumbersome. Therefore, in some embodiments, an adapter 120, such as a luer-lock adapter, may be fitted on the proximal end of the elongated body of the subdural sound 110, with the adapter 120 having a tapered internal channel 122 that has a wider opening in the adapter's proximal end that narrows at the adapter's distal end, and to allow the electrode to more easily fit into the proximal open end of the receiving channel of the sound. In some embodiments, the adapter 120 is also configured to be attached to an irrigation mechanism that delivers fluids through the receiving channel, thus allowing lubricated advancement of the sound through the subdural space and/or lubricated advancement of the electrode through the receiving channel.

In some implementations, the electrode 130 may be constructed from polyimide, Silastic® (a product of Dow Corning Corporation, Midland, Michigan), or any other appropriate electrode substrate material that is safe for contact with brain tissue. The electrode 130 includes n stainless steel contacts or platinum contacts (the number of electrical contacts, n, in an electrode, may be 2, 3, 4, 8, or any other number of electrodes; generally, the number of contacts varies between 4-12). In some embodiments, the electrode may have only one (1) electrode contact. The width of the electrode may be tapered between contacts in order to increase flexibility. In some embodiments, the elongated structure 132 of the electrode 130 may be substantially flat (e.g., a strip-like structure), with a thickness, d, of dimensions 1-2 mm. Generally, extending from each of electrical contacts is a respective electrical wire that can carry measured signals (representative of electrical activity within a brain, or of some other physiological activity in the target area where the electrode is deployed), and may also deliver electrical signals from an electrical source (e.g., a controller in communication with the various electrodes) to control the electrodes or to deliver electrical stimulation to the target area. In some embodiments, electrical signals may be communicated to and from the electrodes via a wireless interface (e.g., a UHF-based transceiver, such as UHF transceivers implemented in passive RFID devices, to allow electrical operation of the devices using power harvested from wireless signals; such wireless transceivers may be configured to operate in other RF bands). In such embodiments, wired electrical connections, such as the wired connections realized using the electrical wires, may not be needed. In some examples, the electrical contacts may be circular contacts, rectangular contacts, or contacts having other geometries and dimensions. An example of an electrical contact that may be disposed on the flat surface of a subdural electrode is a circular (round) contact with a 4 mm diameter. Another example of an electrical contact that is disposed on a subdural electrode is a 2.75 mm×4.57 mm rectangular contact (such dimensions can be used as to provide approximately the same contact area as a 4 mm round contact, but the rectangular contact will have a narrower profile). The contacts may be spaced every 10 mm, or some other appropriate distance. The number of contacts per electrode can vary from 4 up to 12 and possibly more (for example, electrodes configured for brain-computer interfacing use may have hundreds or thousands of electrical contacts). The wires extending from an electrode is generally made as small as possible (1.1 mm). The wires may have unique color codes, and may also include radio-opaque unique identifiers that allow for identification on x-ray.

In some implementations, the elongated body of the electrode may be constructed as a chain of tapered sections. Electrode 162, shown inset 160, is an example of such an electrode. As shown, the electrode 162 may include an elongated structure with a substantially flat contact surface 164 on its contact surface (that is placed tangentially on the target tissue), and includes a chain of body sections (such as the body section 168), with at least some of the body sections including tapered ends along a longitudinal axis of electrode. Each of a plurality of electrical contacts 166a-n is disposed at a respective different one of the body sections.

To further facilitate deployment of multiple electrodes through a single drill hole, in some implementations an electrode inserted through a drill hole may comprise multiple folded electrode strips that define the elongated structure of the electrode. The multiple folded electrode strips are configured to be unfolded for deployment over a target area (e.g., over the cerebral tissue). Upon reaching the destination location (by advancing the electrode through the receiving channel of the subdural sound), the electrode may be actuated (through an electrical or mechanical actuation mechanism) to unfold of the individual folded electrode strips (e.g., by releasing a latch that maintains the electrodes in a folded array, and then causing a rolling motion to unspool or unfold the electrode strips). An example of such a foldable electrode structure (in its unfolded position) is the electrode structure 172 inset 170. In another example implementation, the electrode delivered via the receiving channel of the subdural sound may include an electrode sheet with multiple electrical contacts disposed on the sheet. Such an electrode structure, an example of which is electrode sheet 182 inset 180, can be deployed over a relatively large area of the brain by fitting an edge section of the electrode sheet into the receiving channel of the subdural sound, and advancing the edge section of the electrode sheet through the receiving channel for placement tangential to the target tissue in the subdural space of the patient. Then, another subdural sound is deployed to another target site within the subdural space while the first subdural sound remains at the first target site to anchor the first edge section of the electrode sheet so that it largely remains in place. A second edge section of the electrode sheet is fitted into the receiving channel of second subdural sound, and the edge section is actuated (e.g., pushed) through the receiving channel of the second sound toward the sound's distal end. This process can then be repeated, if necessary for additional edge sections of the electrode sheet until the sheet is fully deployed and spanning the desired surface area over the tissue in the target area. In situations where an electrode sheet is deployed, the subdural sounds used to deploy the sheet will typically have a notch or groove running through at least part of the elongated body of the sound (i.e., the receiving channel would not fully be enclosed within the elongated body).

Target areas where the electrodes may be deployed include, in addition to a patient's brain, other hard to reach areas of the body. Furthermore, the electrodes described herein may also be used as cortical stimulators and cyber-prostheses. In these situations, the electrodes may be placed as part of a permanent prosthesis and not just for temporary monitoring and/or stimulation.

Thus, embodiments of the system 100 include a subdural sound that includes an elongated body configured to be placed within a subdural space of a brain area of a patient, with the elongated body defining a receiving channel, and a curved tip at a distal end of the elongated body, with the curved tip configured for angled insertion into the subdural space (e.g., by wedging it into the subdural space) of the patient to advance the elongated body to a target site in the subdural space. The system further includes an electrode comprising an elongated structure, a plurality of electrical contacts disposed on a substantially flat first side of the elongated structure, with a leading end of the electrode being fitted within a proximal end of the receiving channel of the subdural sound so as to be advanced via the receiving channel, when the subdural sound is placed at the target site within the subdural space, to the target site for tangential placement of the electrode on target tissue in the subdural space. As noted, in some examples, the system 100 also includes an irrigation adapter (such as the adapter 120) coupled to a proximal (trailing) end of the elongated body of the subdural sound, with the irrigation adapter being connectable to an irrigation mechanism, and configured to direct irrigation fluid through the receiving channel defined in the elongated body of the subdural sound to facilitate displacement of subdural sound through the subdural space. In some examples, the system may additionally include a wedge implement (e.g., a "shoehorn-type" implement), schematically depicted as the structure 140 in FIG. 1, to facilitate insertion of the sound into the subdural space at angles, defined by a longitudinal axis of the elongated body and a tangential plane of the subdural space, in a range of, for example, 70°-110°. The wedge implement is configured to receive the curved tip of the subdural sound for slidable displacement of the curved tip across the wedge implement to allow the curved tip to slidably enter the subdural space.

FIG. 1 also includes a photo of an example wedge-implement, provided within inset 142, which may be similar to the implement 140. As illustrated, the wedge implement may include an elongated body 144 with a curved distal end 146. The elongated body 144 of the wedge implement may define an open channel into which the subdural sound can fit (i.e., the channel defined by the elongated body 144 should be dimensioned to accommodate the subdural sound 110). In some embodiments, the channel configuration, in cross-section, is substantially U-shaped. The end portions of the walls of the U-shaped cross-section may be inwardly curved. The distal end 146 of the wedge implement is generally placed near the edges of the hole/opening 102 so that, in operation, a subdural sound can be placed near the proximal end of the wedge implement (or somewhere closer to the middle of the interior channel), and pushed towards the distal end near the hole/opening 102. The wedge may be constructed from a relatively rigid material to resist movement or bending of the subdural sound (in a perpendicular direction opposite the normal to the interior walls of the wedge implement that define the interior channel). Consequently, the wedge implement helps to nudge and fit the subdural sound's elongated body in a direction towards the middle of the burr hole 102 (and away from the wedge implement 140).

Figure 2:
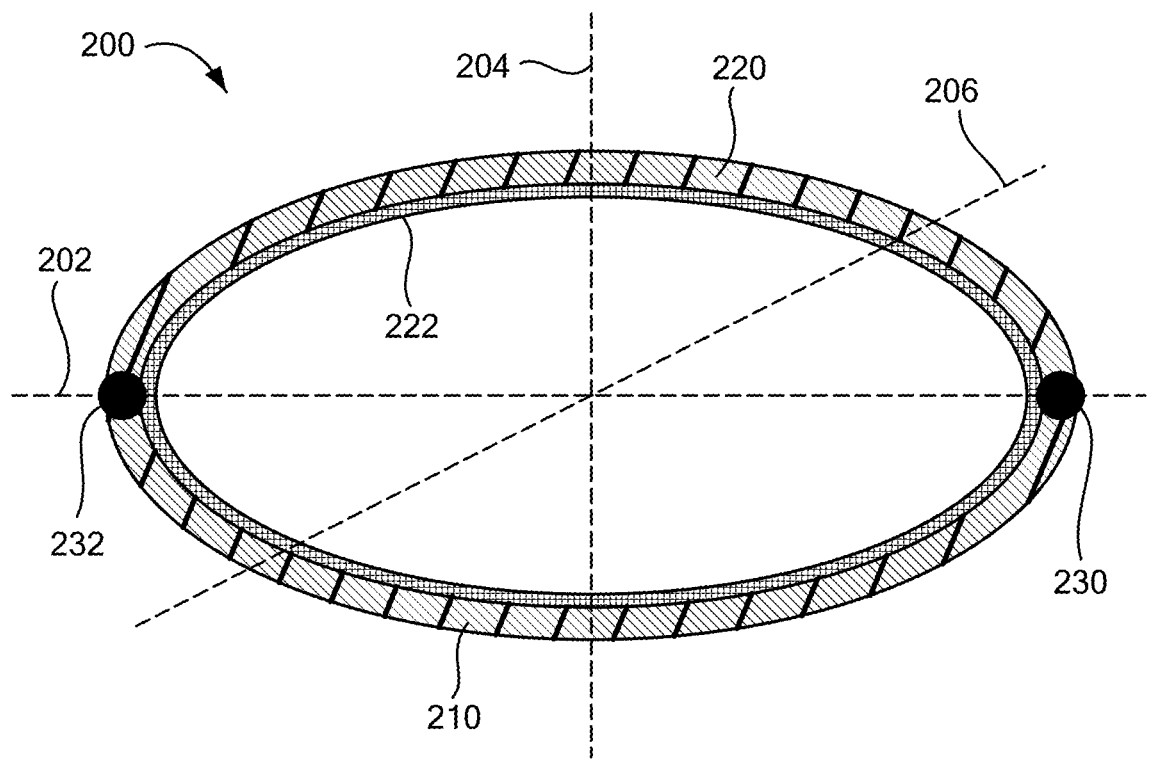
FIG. 2 is a diagram of a cross-sectional view of an example ovalized lumen defined in the subdural sound.

In some implementations, the elongated body of the subdural sound may include an exterior wall that fully encloses, in cross-section, the receiving channel. For example, the elongated body of the subdural sound may be a flexible ovalized lumen defining the receiving channel. FIG. 2 is a diagram of a cross-sectional view 200 of an example ovalized lumen 210 comprising the elongated body of a subdural sound (such as the sound 110 depicted in FIG. 1). The example flexible ovalized lumen 210 includes an exterior oval wall 220, which may be constructed from a braid-reinforced polymer (e.g., stainless steel braid-reinforced polymer), and two support wires 230 and 232 embedded in the exterior oval wall 220 and extending along substantially a length of the subdural sound. The braid-reinforced polymer wall is configured to give the lumen a level of rigidity sufficient to inhibit kinking of the ovalized lumen, thus keeping the receiving channel of the subdural sound open, and providing a substantially unimpeded passage for a subsequently inserted electrode. The support wires embedded in the exterior wall 220 are configured to prevent kinking of the flexible ovalized lumen during advancement of the flexible ovalized lumen in the subdural space. The support wires 230 and 232 cause the elongated body (such as the elongated body 112) to have a reduced level of flexibility in one or more planes defined by the two or more support wires, compared to other planes intersecting the elongated body of the subdural sound, with the reduced level of flexibility in the one or more planes defined by the two or more support wire restricting degree of deflection of the elongated body in the one or more planes while allowing partial deflection of the elongated body in at least one of the other planes intersecting the elongated body. For example, FIG. 2 shows a line 202 which is a segment included in a plane passing through the wires 230 and 232. The rigidity of the support wires constrains the level of flexibility, and as a result the level of deflection, that can be experienced by the elongated body in planes passing through these two points of the wires 230 and 232 (in a 3D space in which the entirety of the elongated body exists, there could be multiple planes that each pass through the shown points of the wires 230 and 232). On the other hand, an illustrated line 204, which is perpendicular to the line 202, and a line 206 are shown as not directly passing through support wires embedded in the exterior wall of the elongated body. The lines 204 and 206 belong to other planes not passing through both of the illustrated wires 230 and 232. Consequently, the level of flexibility and degree of potential deflection of the elongated body in planar directions not including the support wires (such as the wires 230 and 232) will be higher than in planar directions that do include the wires 230 and 232. While FIG. 2 depicts a cross-section of the elongated body with two support wires, additional support wires may be included in the ovalized lumen structure (e.g., if additional rigidity and durability for the elongated body of the subdural sound is required) to cause the elongated body to have a different flexibility and body deflection profile.

The support wires 230 and 232 embedded in the exterior wall of the subdural sound's elongated body (be it an ovalized lumen, or some other cannulated structure) may be constructed using one or more shape-memory materials such as, for example, Nickel Titanium (Nitinol). The support wires 230 and 232 (whether constructed from Nitinol or some other shape-memory material) generally have superelasticity characteristics that allow the elongated body to revert to an initial undeformed position/orientation of the wires following deformation of the wires (e.g., as a result of bending the elongated body comprising the wires). This wire's superelasticity property can supplement the braid-reinforced polymer wall's ability to reduce/inhibit kinking of the elongated body, thus keeping the receiving channel of the subdural sound open to provide a substantially unimpeded passage for a subsequently inserted electrode. The level of deformation of the wires in their initial (resting) orientation, which determines the curving characteristics of the subdural sound (including the extent of the curving of the tip, such as the curved tip 114 illustrated in FIG. 1) can be controlled by applying controlled heating (during the manufacturing process, or at a later point of time) at appropriate temperatures according to the shape-memory material's temperature-based behavior profile.

As further shown in FIG. 2, in some embodiments, the ovalized lumen (or any other cannulated structure that is used to constitute the elongated body 112 of the subdural sound) may include an internal liner wall 222 to protect the exterior wall 220, enhance the structural strength of the elongated body of the subdural sound, and facilitate movement of the electrode as it traverses the receiving channel defined by the exterior wall 220 and/or the liner 222. An example of a liner material that may be used to form the liner wall is polytetrafluoroethylene (PTFE), which has a low coefficient of friction and can thus facilitate movement of an electrode (such as the electrode 130 of FIG. 1) through the receiving channel en route to the target site in the subdural space. Other type of lubricious liner materials may also be used.

Figure 3:
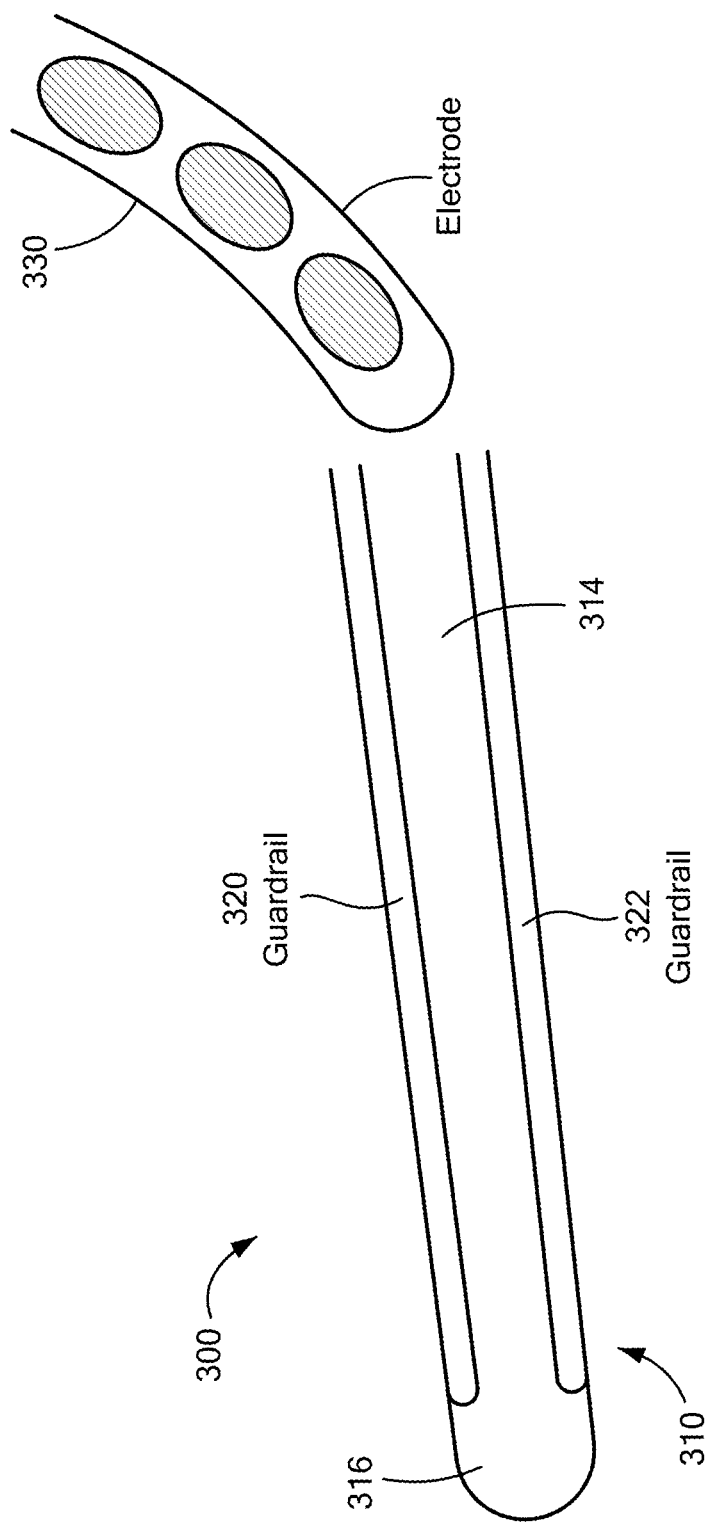
FIG. 3 is a bottom view diagram of a system that includes an example subdural sound device with guardrails.

In some embodiments, the elongated body may use different shapes or configurations to define the exterior wall of the elongated body and/or the interior receiving channel. For example, the elongated body may be substantially rectangular in shape, cylindrical in shape, or may have any other exterior surface configuration that is adapted to facilitate relatively easy entry to, and advancement through, the subdural space in a manner that minimizes (or altogether eliminates) the risk of injury or abrasion of the brain tissue. In another example, the elongated body may define a receiving channel that is not fully enclosed by the exterior of the elongated body. Consider the example embodiment of a subdural sound system 300 illustrated in FIG. 3, which provides a bottom view of a subdural sound 310 that includes guardrails 320 and 322 (which may be integrally extended from an inner surface 314 of an elongated body of the subdural sound 310). The guardrails longitudinally extend along the length of the elongated body up to (but not necessarily including) a tip section 316 (which may be similar to the curved tip 114 of the subdural sound 110 of FIG. 1). The guardrails 320 and 322 define a receiving channel that has an open contact side (i.e., the side that is exposed to, and comes in contact with the brain tissue). The guardrails 320 and 322 may be projections that extend from outer edges of the surface 314 and partially cover the surface 314, thus defining an inner area with a closed side defined by the surface 314, and an open, contact side, defined by the guardrails. An electrode 330 (which may be similar to the electrode 130 of FIG. 1) has its elongated structure fitted within the inner space defined between the guardrails 320 and 322 and the surface 314, and can advance along the guardrails to the target site where the distal end of the subdural sound, or the tip section 316, are located. The surface 314 and the inner walls of the guard rails (facing the surface 314) may be coated with lubricious material (such as PTFE) to facilitate advancement of the electrode 330.

As noted, the subdural sound implementations described herein may be structured so that they include variable rigidity at different parts along the lengths of the elongated body. For example, with reference now to FIG. 4, a top view diagram 400 of a subdural sound 410 (which may be similar to the subdural sound 110 of FIG. 1) that includes a plurality of adjacent regions, with each such region having different rigidity characteristics. In the example of FIG. 4, two regions with different characteristics are illustrated, namely a distal section/region 412 (comprising approximately ⅓ of the total length of the elongated body of the subdural sound 410), and a proximal section 414 that comprises approximately ⅔ of the length of the elongated body. However, the subdural sound's elongated body may comprise any number of separate sections (regions), each with different respective lengths (absolute or relative) and rigidity characteristics. As shown, in the example subdural sound 410 of FIG. 4, the distal region 412 is implemented so that it softer than the proximal section 414 (i.e., the distal region 412 has a lower stiffness level than that of the proximal section 414). In some embodiments, the varying rigidity/stiffness characteristics of different sections can be controlled, for example, by varying the density of the braided reinforced materials used to form an exterior wall 430, e.g., through an extrusion process, which would also facilitate the formation of a receiving channel 432, represented by dashed lines, within the interior of the subdural sound 410.

As further shown in FIG. 4, and as similarly illustrated in FIG. 1, an adapter 420 (e.g., an irrigation adapter such as a luer-lock adapter) with a tapering channel 422 that has a narrow opening (at the end portion that attaches to the subdural sound) that is typically narrower than the diameter of the receiving channel 432, thus allowing an electrode fitted within the wider end of the adapter to easily be threaded (inserted) into the subdural sound's receiving channel. The adapter 420 is generally compatible with standard syringes for flushing a device lumen, in this case the receiving channel of the subdural sound. The adapter 420 is also couplable to an irrigation mechanism (not shown in FIG. 4, but partially illustrated in FIG. 7 as discussed below) that delivers irrigation fluid via the receiving channel of the sound in order to irrigate the area surrounding the progressing structure. Irrigation fluid introduced into the inner channel of the sound can exit through the distal opening of the sound (e.g., the same opening through which an electrode fitted through the receiving channel emerges), or through one or more other perforations or openings formed in the elongated body of the subdural sound. Irrigation fluid can be introduced via a syringe coupled to the adapter (e.g., the adapter 120 or 420), which directs the irrigation fluid via the adapter's internal channel, to the receiving channel of the subdural sound, and out at the distal opening of the sound, thus lubricating the surface of the target area (e.g., brain), and the path thereto, during advancement of the sound through the subdural space. Irrigation fluid may also be introduced during deployment of an electrode through the sound's receiving channel. Irrigation fluids flow under pressure delivered by an external syringe or pump through the receiving channel, exiting through the sound's distal opening. In some embodiments, the adapter can also be in mechanical communication with a supplemental guiding mechanism (e.g., catheter, or a scope-based device) to mechanically actuate the adapter, and thus mechanically actuate the subdural sound or electrode fitted through the receiving channel of the sound (e.g., if auxiliary force or torque is required to nudge the sound or electrode).

With continued reference to FIG. 4, extending from the distal end of the distal section 412 is a tip section (marked as an atraumatic tip) 440 which may a separate (non-integral) structure attachable to the distal section 412, or may be integrally connected to the distal section 412, and manipulated to have a particular shape or structure by, for example, a controlled heating process, a shape-form process, etc. In some examples, the tip 440 is not braid-reinforced and is therefore the softest region of the device, to ensure atraumatic use. The entire usable structure constituting the subdural sound 410 may include hydrophilic coating to reduce friction in the subdural space.

While FIG. 4 shows the subdural sound 410 has a distinct tip section 440, in some embodiments the curved portion of the subdural sound may be formed by bending the distal section (bending of the distal section may also be done in addition to having a distinct tip section such as the tip section 440). The bending of the distal section (or any of the other sections of the elongated body of the subdural sound) may be performed by causing the shape-memory support wires to be bent at a temperature at which the support wires would remain at their bent orientation. For example, and as illustrated in FIG. 5, a side view 500 of an example subdural sound 510, coupled at one of its ends to an adapter 520 (which may be similar to the adapter 120 or the adapter 420 depicted in FIGS. 1 and 4, respectively) is shown. Similar to the subdural sound embodiment depicted in FIG. 4, the subdural sound 510 is also shown as including two separate sections, namely the distal section 512, which is connected at its distal end to a tip section 540, and a proximal section connected (e.g., integrally, or through some fastening mechanism) to the distal section 512. The distal section 512 is shown as being bent so that its distal end (where the tip 540 attaches to the distal section 512) is at approximately and 80°-90° angle relative to longitudinal axis of the proximal section 514 of the elongated body of the subdural sound. Curving the distal section 512 of the subdural sound can allow to better position the tip 540 for entry into the subdural space under the skull.

To maintain the distal section in its bent shape, the distal section may be heat bent while the elongated body of the subdural sound is at a temperature at which the shape-memory support wires (an embedded support wire 518 is shown, as a dashed line, extending along the length of the elongated body of the subdural sound comprising the distal section 512 and the proximal section 514) can be deformed and maintain their deformed shape.

The example embodiments of the subdural sounds depicted in FIGS. 1-5 may be fabricated using the following materials listed in Table 1 below:

TABLE 1

| Component (as referenced in FIGS. 4 and 5) | Material |
|---|---|
| Polymer wall, proximal stiff portion (e.g., the sections 414 and 514 of FIGS. 4 and 5) | Pebax polymer, 40D durometer |
| Polymer wall, distal soft portion (e.g., the sections 412 and 512 of FIGS. 4 and 5) | NeuSoft thermoplastic polyurethane, 62A durometer |
| Polymer wall, tapered tip (e.g., the tips 440 and 540 of FIGS. 4 and 5) | Pebax polymer with 20% BaSO4 (radiopaque), 35D Pebax |
| ID Liner (e.g., the liner 222 of FIG. 2) | PTFE film |
| Braid reinforcement | Stainless steel wire braid |
| Axial support wires (e.g., the wires 230 and 232 of FIG. 2, or the wire 518 of FIG. 5) | Superelastic nitinol (could be shape memory) |
| Luer adaptor (e.g., the adapter 120 of FIG. 1, or adapters 420 and 520 of FIGS. 4 and 5) | SLA resin (3D printed part, but could be molded ABS or similar plastic) |
| Hydrophilic coating | Urethane hydrophilic coating with primer |

Figure 6:
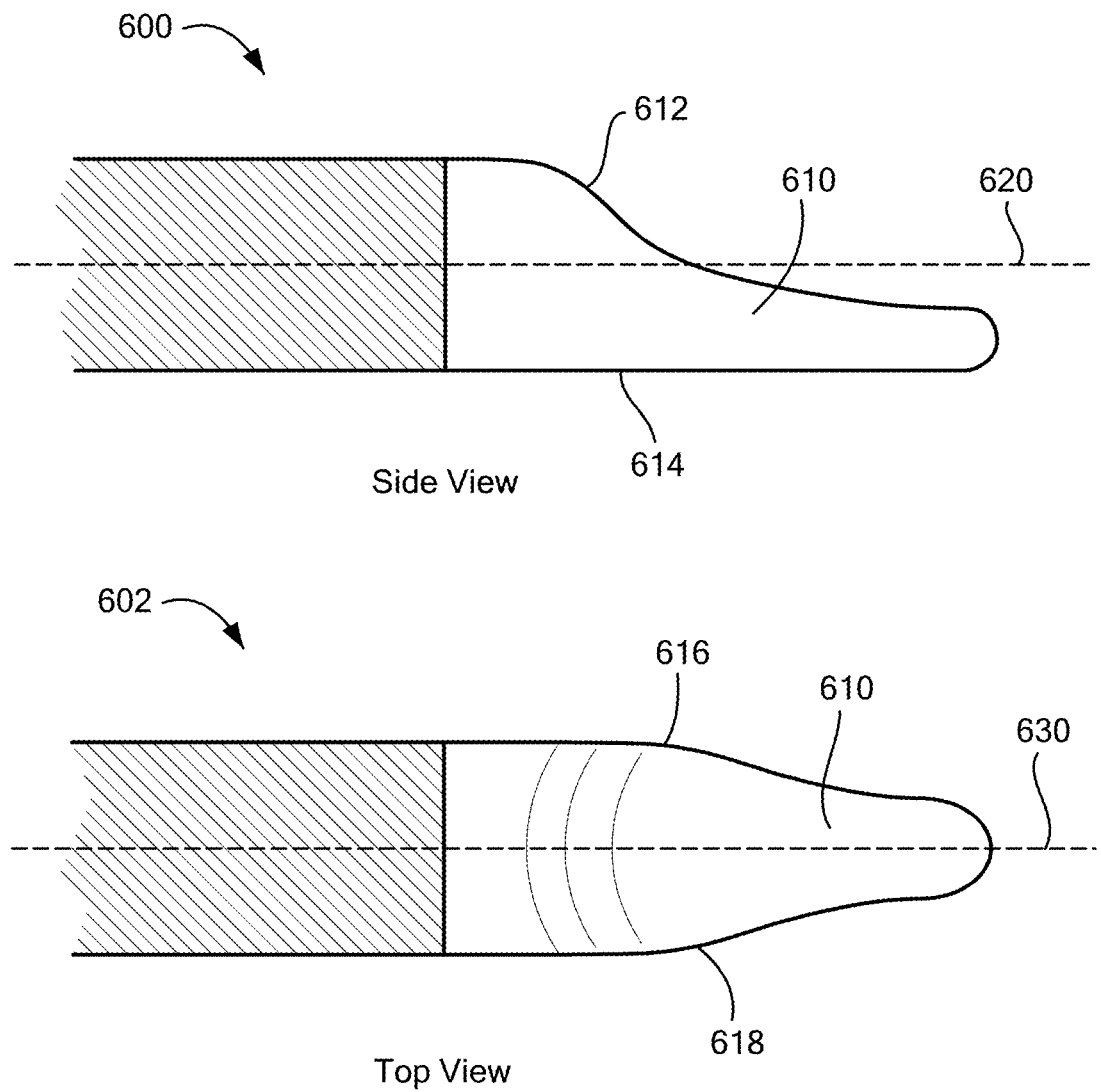
FIG. 6 includes a side view and a top view of an example tip that may be included with subdural sound devices described herein.

As noted, the curved tip (or "tip section," or simply "tip") may integrally extend from the distal section of the elongated body constituting the subdural sound, and typically is fabricated so that it softer than other portions of the elongated body (to render the tip as an atraumatic tip). The curved tip can be shaped-set by bending or manipulating a portion of the elongated body (comprising embedded shape-memory wires such as the wires 230 and 232 depicted in FIG. 2) into the desired or required shape. An example of a shape-set curved tip, or curved portion, is the curved tip 114 of the subdural sound 110 of FIG. 1, or the distal section 512 of FIG. 5 (on which a further tip section is fitted). Such shape-setting procedure would typically be done at a temperature that is equal to or exceeds a shape-set temperature at which bent shape memory materials would not revert to their pre-deformed shape upon applying the bending force. In some examples, more complex-shaped tips, that are configured to allow easy insertion of the subdural sound into the subdural space, and to reduce likelihood of injury of the brain tissue or any other part of the patient's head, may be formed or fitted onto the subdural sound. For example, consider FIG. 6 showing an example embodiment of a tip 610, as seen in a side view diagram 600 and a top view diagram 602. The tip 610 depicted in FIG. 6 may have been pressed shaped or molded from the distal end of the elongated body. Alternatively, the tip 610 may be a non-integral piece that was separately fabricated (from a material that is generally softer than the material forming the elongated body of the subdural sound), and is fitted (through threading, welding, or some other attachment procedure) to the distal end of the elongated body of the subdural sound. In some embodiments, the tip material is radiopaque and may be formed with a soft polymer doped with 20% BaSO4 to provide visualization of the distal end of the device during the procedure.

In some embodiments, the tip 610 may be tapered in one or more of its sides to further facilitate insertion or wedging of the subdural sound into the subdural space. For example, as further shown in FIG. 6, the tip 610 may include a first side (side 612, as shown in the side view diagram 600) with a curving profile defined in relation to a first axis 620 of the elongated body, a second side (side 614, as shown in the side view diagram 600) with a substantially flat profile in relation to the first axis, and third and fourth sides (sides 616 and 618 shown in the top view diagram 602) defining a tapering profile in relation to a second axis 630 of the elongated body.

Figure 7:
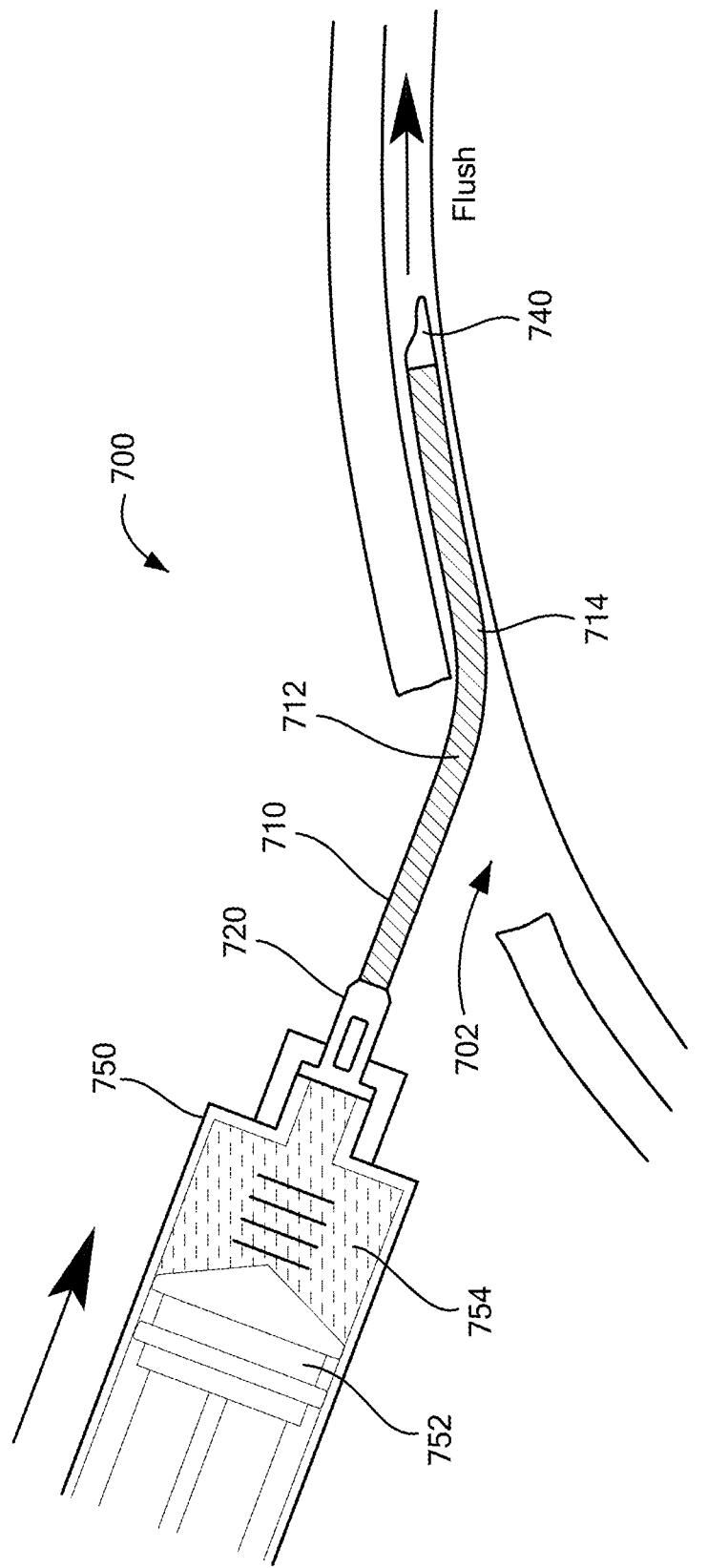
FIG. 7 is a diagram of an example system comprising a subdural sound inserted and displaced within the subdural space to deploy subdural electrodes.

Operation of the embodiments of the subdural sound devices, such as those depicted in FIGS. 1-6, will next be described with reference to FIG. 7, providing a diagram 700 of an example system comprising a subdural sound inserted and displaced within the subdural space to deploy subdural electrodes. The procedure for placing electrodes in the subdural space, using subdural sounds such as those described herein, begins with making a 3-4 cm incision in the area of interest. The incision sizes may be bigger or smaller depending on the particular application for which the burr-hole is required. Alternatively, other procedures that provide access to the skull (i.e., by means other than making an incision) may be used. Subsequently, a high-speed drill is used to create a drill hole 702 that is 15-20 mm in diameter. After hemostasis is obtained the dura is opened in a stellate fashion. A subdural sound 810, which may be similar to the sound 110 depicted in FIG. 1, is then directed into the subdural space in the desired direction, assisted by the bent configuration of a distal section 714 and/or a separate curved tip 740 (which may be structured/shaped in a manner similar to the tip 610 shown in FIG. 6), to allow the sound device to negotiate the sharp angle defined between the normal to the opening of the drill hole 702 and a tangential plane of exposed subdural space tissue. To further facilitate the initial insertion of the subdural sound through the burr-hole, a wedge implement (also referred to as a "shoehorn device"), such as the device 140 depicted in FIG. 1, may be used to wedge the device between the interior of skull and the subdural space tissue, and to allow the sound device to be slidably guided into the subdural space.

The passage of the sound may be monitored with intra procedural x-ray, fluoroscopy, or any other imaging technology, as well as through tactile or in some embodiments visual or electrochemical feedback. When the subdural sound has reached the intended position, the appropriate length electrode is selected based, for example, on the observed/determined length markings on the sound device. While care is taken that the sound is stabilized, an electrode (such as the electrode 130 of FIG. 1) is fitted into a proximal opening at the proximal (trailing) end of the sound, and the electrode is then advanced within the receiving channel defined in the elongated body of the subdural sound to its final position in the subdural space, where the leading end of the electrode exits the opening at the distal end of the subdural sound. The fitting of an electrode (not shown in FIG. 7) can be facilitated by using an adapter 720 (which may be similar to the adapter 120 depicted in FIG. 1) coupled to the proximal end of the subdural sound 710. As noted, the adapter may have a tapered internal channel (such as the channel 122 shown in FIG. 1) with a wider opening at the end of the adapter not coupled to the subdural sound. An electrode is fitted through that wider end, and is funneled by the narrowing diameter of the adapter's channel into the receiving channel of the subdural sound.

The adapter 720 is also couplable, at its other end, to an irrigation mechanism (in this case, a syringe 750 with a plunger 752 to push irrigation fluid 754, although other irrigation mechanisms may be used) configured to deliver the irrigation fluid 754 (provided from an irrigation fluid source, not shown in FIG. 7) via the internal cannula of the adapter, to the receiving channel of the subdural sound device. The irrigation fluid lubricates the walls of the receiving channel of the sound, thus facilitating advancement of the electrode within the interior of the subdural sound. The irrigation fluid also acts to lubricate the area outside of the subdural sound 710, thus facilitating passage of the sound through the subdural space. Particularly, the irrigation fluid passes through the receiving channel of the sound, and exits at the distal open end of the sound (be it at the distal end of the distal section 714, or the distal end of the tip 740). In such embodiments, the sound may be initially fitted through the burr hole to negotiate the initial sharp angle that places the subdural sound at a substantial tangential position relative to the surface of the dura mater tissue in the subdural space. Before the sound is advanced to the destination site, an electrode may be fitted through the irrigation adapter 720, and an irrigation mechanism is then fitted onto the adapter. The subdural sound can then be pushed (manually, or using an electromechanical actuator to apply force to advance the subdural sound through the subdural space), with intermittent flushing of irrigation fluid to facilitate the traversing of the subdural sound to the destination site. It is to be noted that, in some situations, the irrigation mechanism may be connected to the subdural sound before the electrode is fitted into the subdural sound, in order to first facilitate advancing the sound to its destination location in the subdural space, then removing the irrigation mechanism, and fitting the electrode to the receiving channel (possibly through the tapered channel of the adapter 720). Thus, advancement of the electrode within the receiving channel of the sound can be done with or without use of irrigation fluids. As noted, different types of subdural electrodes may be deployed through the procedures described herein, including the electrode strips 130, 152, and 162 depicted in FIG. 1, as well as the folded multi-strip electrode 172 (which advances through the receiving channel of the subdural sound in a folded configuration, and is unfolded upon being deployed outside the receiving channel), the electrode sheet 182 (that can span a sizable portion of the tissue in the subdural space), and other types and shapes of the subdural electrodes.

After the subdural sound has reached its destination, the subdural sound is optionally withdrawn (although in some embodiment it may be maintained, at least temporarily, to help anchor the electrode to the target tissue without injuring the tissue) and the appropriate position of the electrode may be confirmed with x-ray or fluoroscopy. Withdrawal of the subdural sound can be performed (typically after removal of the irrigation mechanism and/or the irrigation adapter) by applying moderate outward pulling force on the subdural sound and/or applying inward force to a tail end portion of the electrode that has been fitted through the receiving channel of the subdural sound (if a tail end portion of the electrode can be gripped). The same, or different, subdural sound, and the same placement procedure can be repeated to tangentially place the next sound and/or electrode on the tissue in the subdural space. When all subdural electrodes have been placed, the drill hole may be sealed with a polymer sealant such as Duraseal™ or a silastic burr hole cover so as to minimize the risk of cerebrospinal fluid leakage through the tunneling sites.

Figure 8:
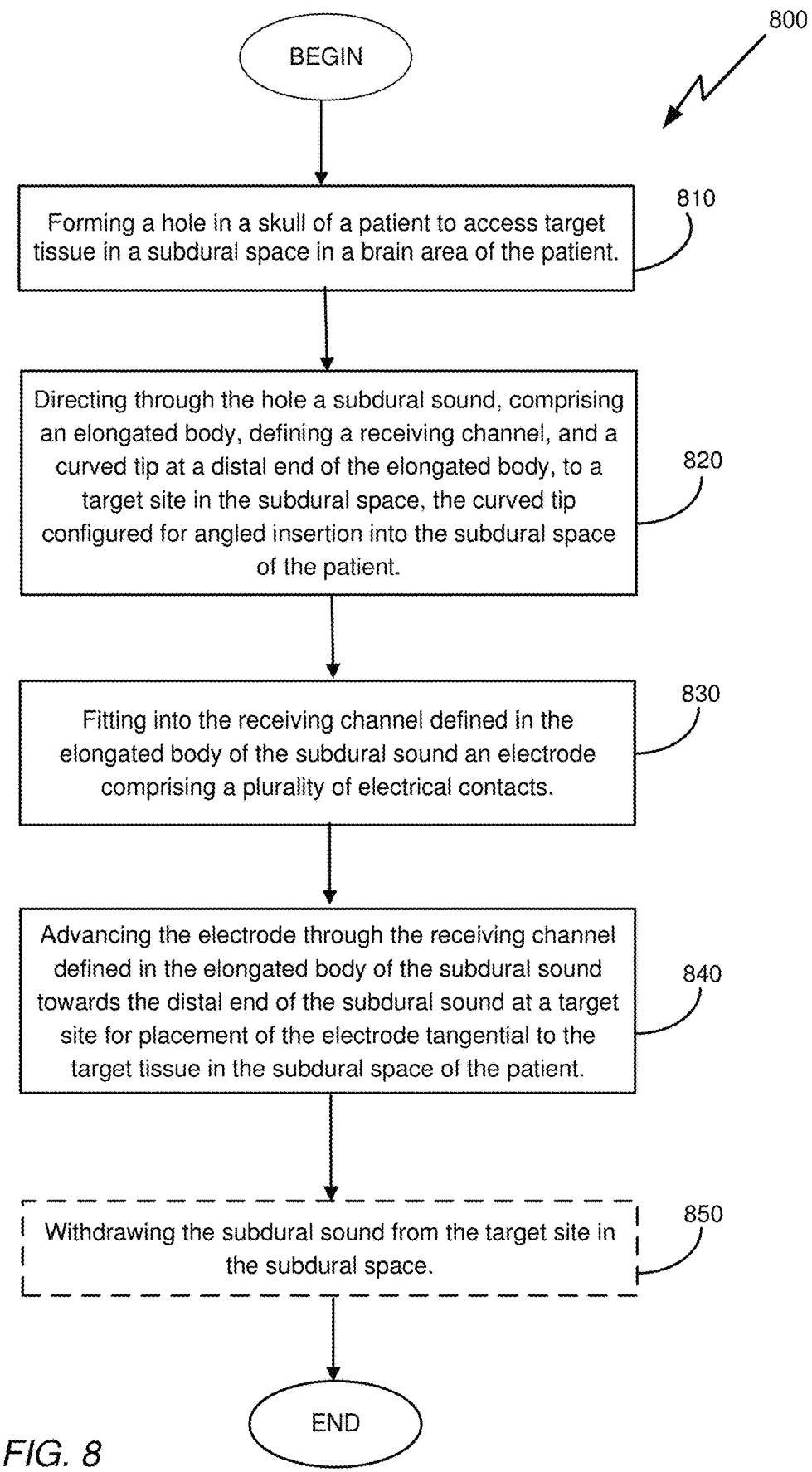
FIG. 8 is a flowchart of an example procedure to place electrodes.

Further details regarding the electrode placement procedures are provided with reference to FIG. 8, showing a flowchart of a procedure 800 for tangential placement of electrodes in the subdural space (or in other hard-to-reach locations of a patient's body). The procedure 800 includes forming 810 a hole in a skull of a patient to access target tissue in a subdural space in a brain area of the patient. The procedure 800 additionally includes directing 820 through the hole a subdural sound (such as the sound device 110 and/or 710 depicted in FIGS. 1 and 7, respectively), comprising an elongated body, defining a receiving channel, and a curved tip at a distal end of the elongated body, to a target site in the subdural space, with the curved tip configured for angled insertion into the subdural space of the patient.

The procedure 800 additionally includes fitting 830 into the receiving channel defined in the elongated body of the subdural sound an electrode comprising a plurality of electrical contacts, and advancing 840 the electrode through the receiving channel defined in the elongated body of the subdural sound towards the distal end of the subdural sound at a target site for placement of the electrode tangential to the target tissue in the subdural space of the patient.

The procedure 800 may also include withdrawing the subdural sound from the subdural space (illustrated as optional operation 850). For example, withdrawing the subdural sound may include withdrawing the subdural sound while applying pressure to a proximal end of the electrode to keep the electrode in the tangential placement at the target tissue, and repeating the directing, fitting, and advancing for one or more other subdural sounds and/or for one or more electrodes, at respective one or more locations in the subdural space to form an electrode array spanning at a least a portion of a dura mater tissue in the patient's brain. In such embodiments, the repeating the directing, fitting, and advancing for one or more other subdural sounds and/or for one or more electrodes to form the electrode array may include deploying the electrode array to form one or more of, for example, a brain-computer interface, or a brain disorder (e.g., epilepsy) monitoring and treating array.

As noted, the sound can be used to determine the electrode length needed to be placed into the subdural space at the destination site. In such embodiments, directing the subdural sound to the target tissue may include determining penetration distance of the subdural sound into the subdural space based on markings disposed on the elongated body of the subdural sound, and fitting one of a plurality of available electrodes with a length selected based on the determined penetration distance.

In some examples, the procedure 800 may further include delivering irrigation fluid via an irrigation adapter (e.g., the adapter 120 or 720 depicted in FIGS. 1 and 7, respectively) coupled to a proximal end of the elongated body of the subdural sound, and through the receiving channel defined in the elongated body of the subdural sound.

In embodiments in which the electrode includes multiple folded electrode strips (such as the electrode 172 depicted in FIG. 1), the procedure 800 may further include unfolding the multiple folded electrode strips to deploy the unfolded electrode strips over the target tissue. In embodiments in which the electrode includes an electrode sheet with multiple electrical contacts disposed on the sheet (such as the electrode sheet 182 of FIG. 1), the fitting operation may include fitting a first edge section of the electrode sheet into the receiving channel of the subdural sound, and advancing the first edge section of the electrode sheet through the receiving channel for placement of the first edge section of the electrode tangential to the target tissue in the subdural space of the patient. In such embodiments, the procedure additionally includes directing another subdural sound through the hole for placement of the other subdural sound at another location in the subdural space of the patient while the first subdural sound remains at the target site to anchor the first edge section at substantially the target tissue, fitting another edge section of the electrode sheet into another receiving channel of the other subdural sound, and advancing the other edge section of the electrode sheet to the other location in the subdural space of the patient.

The procedure 800 may additionally include fitting a wedge implement (such as the implement 140 FIG. 1) through the hole, with the wedge implement configured to facilitate insertion of the elongated body to the subdural space at angles, formed by a longitudinal axis of the elongated body and a tangential plane of the subdural space, in a range of 70°-110°. In such embodiments, directing through the hole the subdural sound may include placing the curved tip on the wedge implement fitted through the hole, and slidably displacing the curved tip across the wedge implement to allow the curved tip to slidably enter the subdural space.

Figure 9:
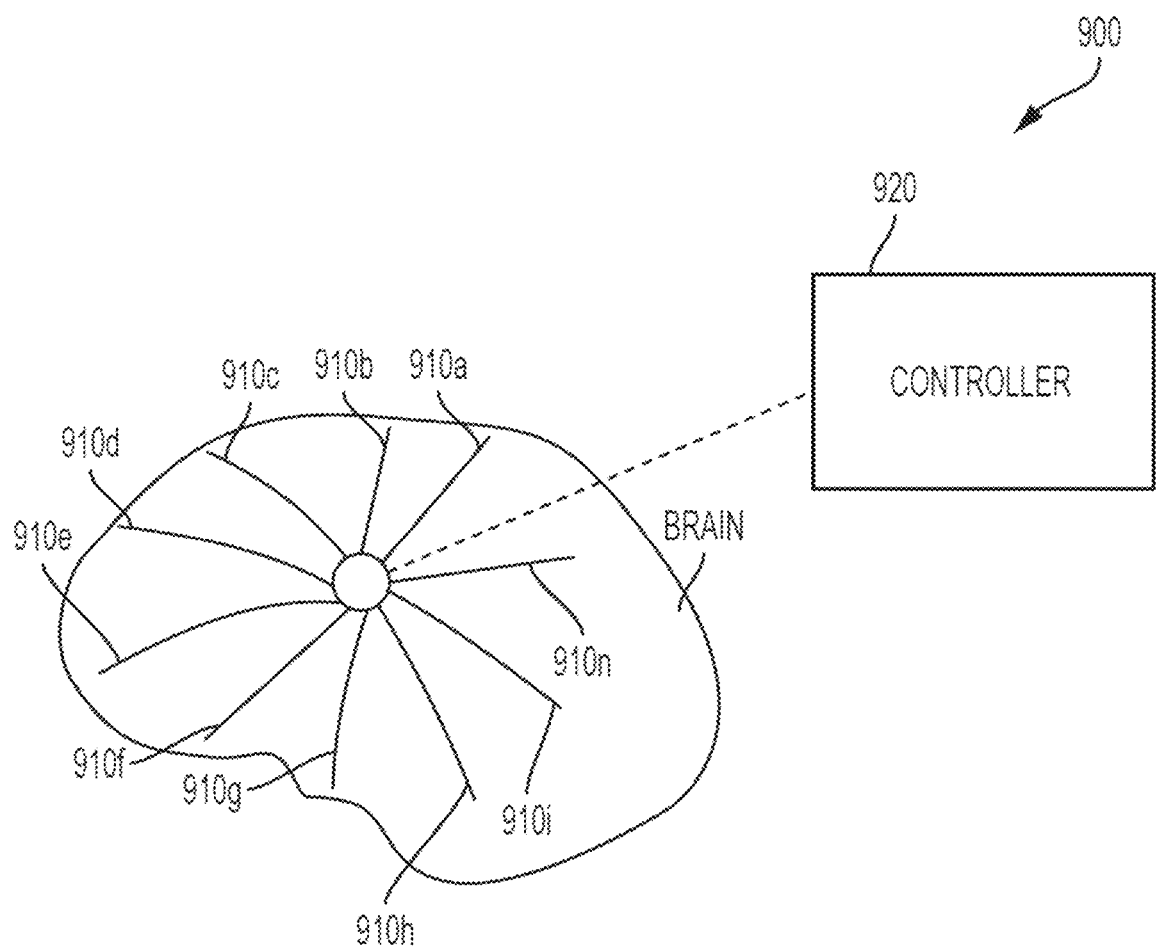
FIG. 9 is a diagram illustrating an example deployment of multiple electrodes.

Turning next to FIG. 9, a diagram 900 showing the resultant deployment of multiple electrodes 910$a$-$n$ following performance of an electrode-placement procedure (such as the procedure 800 described in relation to FIG. 8) is provided. The placement of the multiple electrodes 910$a$-$n$ can be achieved, in some embodiments, based on the narrow electrode profile that allows placement of multiple electrodes through a small skull opening. As illustrated in FIG. 9, the deployment of the multiple electrodes is based, in this example, on a radial scheme that is used to cover a large portion of the cerebral hemisphere using a small exposure. The particular deployment/distributive scheme that is used can be tailored to each individual patient, using, in each case, small exposure and multiple electrodes. Thus, any desired type of configuration (non-radial configuration, non-symmetrical configurations, etc.) may be used. The configuration used may be such where the electrodes are directed to various predetermined locations at the subdural space (or other locations within a body of a patient) for placement therein, with the tail end of the electrodes not necessarily being near the drill hole. That is, an electrode may be placed at a location where its tail end substantially far from the drill hole. A controller 920 is in electrical communication with the electrode contacts on the multiple electrodes. Such electrical communication may be established, in some embodiments, via wired electrical connections. Alternatively, the electrical communication between the controller 920 and the electrical contacts of the electrodes 910$a$-$n$ can be performed using wireless communication, achieved using wireless transceivers included with the controller 920, and with the various electrical contacts disposed on the multiple electrodes (in some embodiments, one transceiver per electrode may be provided, with that transceiver then having direct electrical communication with the various electrode contacts on the respective electrode). The controller 920 is configured to collect measurements of electrical activities obtained through the electrode contacts, and/or to controllably send electrical signals (to cause electrical stimulation) to one or more of the electrode contacts. The controller 920 may also be configured to process signals it receives, and/or communicate measurements it receives to a remote device that performs further processing. In some embodiments, the controller 920 may be a processor-based controller, a state-machine controller, or any other type of controller. The controller 920 may also include a memory storage device to store data (e.g., measurement data collected from the various electrode contacts) and or programmable instructions to be executed on a processor, filtering circuitry (to filter or suppress signals that may cause adverse effects to the patient), a communication module (such as a transceiver), a power source (e.g., to operate the controller's circuitry, and/or to transmit electrical stimulation signals to various electrode contacts), and other circuits, modules, and components to operate the controller 920.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate in the context of the systems, devices, circuits, methods, and other implementations described herein.

As used herein, including in the claims, "or" as used in a list of items prefaced by "at least one of" or "one or more of" indicates a disjunctive list such that, for example, a list of "at least one of A, B, or C" means A or B or C or AB or AC or BC or ABC (i.e., A and B and C), or combinations with more than one feature (e.g., AA, AAB, ABBC, etc.). Also, as used herein, unless otherwise stated, a statement that a function or operation is "based on" an item or condition means that the function or operation is based on the stated item or condition and may be based on one or more items and/or conditions in addition to the stated item or condition.

Although particular embodiments have been disclosed herein in detail, this has been done by way of example for purposes of illustration only, and is not intended to be limiting with respect to the scope of the appended claims, which follow. Features of the disclosed embodiments can be combined, rearranged, etc., within the scope of the invention to produce more embodiments. Some other aspects, advantages, and modifications are considered to be within the scope of the claims provided below. The claims presented are representative of at least some of the embodiments and features disclosed herein. Other unclaimed embodiments and features are also contemplated.

What is claimed is:

1. A subdural sound comprising:
   an elongated body configured to be placed within a subdural space of a brain area of a patient, the elongated body defining a receiving channel to receive a displaceable electrode to be tangentially placed at a target site in the subdural space; and
   a curved tip at a distal end of the elongated body, the curved tip configured for angled insertion into the subdural space of the patient to advance the elongated body to the target site in the subdural space,
   wherein the elongated body comprises a flexible ovalized lumen defining the receiving channel, the flexible ovalized lumen comprising an exterior oval wall constructed from a braid-reinforced polymer, with two or more support wires embedded in the exterior oval wall and extending along substantially a length of the subdural sound, the two or more support wires configured to prevent kinking of the flexible ovalized lumen during advancement of the flexible ovalized lumen in the subdural space.

2. The subdural sound of claim 1, wherein the two or more support wires cause the elongated body to have a reduced level of flexibility in one or more planes defined by the two or more support wires, compared to other planes intersecting the elongated body of the subdural sound, with the reduced level of flexibility in the one or more planes defined by the two or more support wires restricting degree of deflection of the elongated body in the one or more planes while allowing partial deflection of the elongated body in at least one of the other planes intersecting the elongated body.

3. The subdural sound of claim 1, wherein the two or more support wires are constructed using one or more shape-memory materials.

4. The subdural sound of claim 1, wherein the elongated body comprises an exterior wall fully enclosing, in cross-section, the receiving channel.

5. The subdural sound of claim 1, wherein the elongated body comprises a plurality of adjacent regions along a length of the subdural sound, the plurality of adjacent regions each having respective different rigidity characteristics, wherein a distal portion of the elongated body is more flexible than another portion of elongated body.

6. The subdural sound of claim 1, wherein the curved tip includes a first side with a curving profile defined in relation to a first axis of the elongated body, a second side with a substantially flat profile in relation to the first axis, and third and fourth sides defining a tapering profile in relation to a second axis of the elongated body.

7. The subdural sound of claim 1, wherein the subdural sound further comprises a distance determination mechanism configured to indicate penetration distance of the subdural sound into the subdural space.

8. A system comprising:
   a subdural sound including:
   an elongated body configured to be placed within a subdural space of a brain area of a patient, the elongated body defining a receiving channel; and
   a curved tip at a distal end of the elongated body, the curved tip configured for angled insertion into the subdural space of the patient to advance the elongated body to a target site in the subdural space; and
   an electrode comprising an elongated structure, a plurality of electrical contacts disposed on a substantially flat first side of the elongated structure, wherein a leading end of the electrode is fitted within a proximal end of the receiving channel of the subdural sound so as to be advanced via the receiving channel, when the subdural sound is placed at the target site within the subdural space, to the target site for tangential placement of the electrode on target tissue in the subdural space,
   wherein the elongated body of the subdural sound comprises a flexible ovalized lumen defining the receiving channel, wherein the flexible ovalized lumen comprises an exterior oval wall constructed from a braid-reinforced polymer, with two or more support wires embedded in the exterior oval wall and extending along substantially a length of the subdural sound, the two or more support wires configured to prevent kinking of the flexible ovalized lumen during advancement of the flexible ovalized lumen in the subdural space.

9. The system of claim 8, wherein the two or more support wires cause the elongated body to have a reduced level of flexibility in one or more planes defined by the two or more support wires, than in other planes intersecting the elongated body of the subdural sound, with the reduced level of flexibility in the one or more planes defined by the two or more support wire restricting degree of deflection of the elongated body in the one or more planes while allowing partial deflection of the elongated body in at least one of the other planes intersecting the elongated body.

10. The system of claim 8, wherein the curved tip includes a first side with a curving profile defined in relation to a first axis of the elongated body, a second side with a substantially flat profile in relation to the first axis, and third and fourth sides defining a tapering profile in relation to a second axis of the elongated body.

11. The system of claim 8, wherein the electrode comprises multiple folded electrode strips defining the elongated structure, the multiple folded electrode strips configured to be unfolded for deployment over the target tissue in the subdural space.

12. The system of claim 8, further comprising: an irrigation adapter coupled to a proximal end of the elongated body of the subdural sound, the irrigation adapter being connectable to an irrigation mechanism, and configured to direct irrigation fluid through the receiving channel defined in the elongated body of the subdural sound to facilitate displacement of subdural sound through the subdural space.

13. The system of claim 8, further comprising: a wedge implement configured to facilitate insertion of the elongated body of the subdural sound into the subdural space at angles, formed by a longitudinal axis of the elongated body and a tangential plane of the subdural space, in a range of 70°-110°, the wedge implement configured to receive the curved tip of the subdural sound for slidable displacement of the curved tip across the wedge implement to allow the curved tip to slidably enter the subdural space.

14. A system comprising: a subdural sound including: an elongated body configured to be placed within a subdural space of a brain area of a patient, the elongated body defining a receiving channel; and a curved tip at a distal end of the elongated body, the curved tip configured for angled insertion into the subdural space of the patient to advance the elongated body to a target site in the subdural space; and an electrode comprising an elongated structure, a plurality of electrical contacts disposed on a substantially flat first side of the elongated structure, wherein a leading end of the electrode is fitted within a proximal end of the receiving channel of the subdural sound so as to be advanced via the receiving channel, when the subdural sound is placed at the target site within the subdural space, to the target site for tangential placement of the electrode on target tissue in the subdural space, wherein the electrode comprises multiple folded electrode strips defining the elongated structure, the multiple folded electrode strips configured to be unfolded for deployment over the target tissue in the subdural space.

15. A system comprising: a subdural sound including: an elongated body configured to be placed within a subdural space of a brain area of a patient, the elongated body defining a receiving channel; and a curved tip at a distal end of the elongated body, the curved tip configured for angled insertion into the subdural space of the patient to advance the elongated body to a target site in the subdural space; and an electrode comprising an elongated structure, a plurality of electrical contacts disposed on a substantially flat first side of the elongated structure, wherein a leading end of the electrode is fitted within a proximal end of the receiving channel of the subdural sound so as to be advanced via the receiving channel, when the subdural sound is placed at the target site within the subdural space, to the target site for tangential placement of the electrode on target tissue in the subdural space, wherein the system further comprises: a wedge implement configured to facilitate insertion of the elongated body of the subdural sound into the subdural space at angles, formed by a longitudinal axis of the elongated body and a tangential plane of the subdural space, in a range of 70°-110°, the wedge implement configured to receive the curved tip of the subdural sound for slidable displacement of the curved tip across the wedge implement to allow the curved tip to slidably enter the subdural space.

* * * * *